United States Patent
Eemeta et al.

(10) Patent No.: US 8,840,876 B2
(45) Date of Patent: Sep. 23, 2014

(54) ANTIMICROBIAL POLYMER COMPOSITIONS AND THE USE THEREOF

(75) Inventors: Modesto Eemeta, Princeton Junction, NJ (US); Robert Di Luccio, Asbury, NJ (US); Xintian Ming, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 2178 days.

(21) Appl. No.: 11/132,543

(22) Filed: May 19, 2005

(65) Prior Publication Data

US 2006/0263329 A1    Nov. 23, 2006

(51) Int. Cl.
| | |
|---|---|
| *A61L 27/34* | (2006.01) |
| *A61L 17/14* | (2006.01) |
| *A61L 17/12* | (2006.01) |
| *A01N 47/44* | (2006.01) |
| *A01N 25/10* | (2006.01) |
| *A61L 29/06* | (2006.01) |
| *A61L 31/14* | (2006.01) |
| *A61L 29/14* | (2006.01) |
| *A61L 27/18* | (2006.01) |
| *A61L 27/50* | (2006.01) |
| *A61L 31/06* | (2006.01) |

(52) U.S. Cl.
CPC .................. *A61L 27/18* (2013.01); *A61L 29/06* (2013.01); *A61L 31/14* (2013.01); *A61L 29/14* (2013.01); *A61L 27/50* (2013.01); *A61L 31/06* (2013.01); *A61L 17/145* (2013.01)
USPC ........................... 424/78.37; 514/634; 554/53

(58) Field of Classification Search
CPC ........ A01N 25/10; A01N 47/44; A61L 17/12; A61L 27/34
See application file for complete search history.

(56) References Cited

U.S. PATENT DOCUMENTS

| | | | | |
|---|---|---|---|---|
| 2,362,511 | A * | 11/1944 | Teeters ........................... | 528/361 |
| 3,636,956 | A * | 1/1972 | Schneider ...................... | 606/224 |
| 3,839,297 | A | 10/1974 | Wasserman et al. | |
| 3,912,692 | A * | 10/1975 | Casey et al. ................... | 528/354 |
| 3,942,532 | A | 3/1976 | Hunter et al. | |
| 3,982,543 | A * | 9/1976 | Schmitt et al. ................ | 606/230 |
| 4,027,676 | A | 6/1977 | Mattei | |
| 4,185,637 | A | 1/1980 | Mattei | |
| 4,201,216 | A | 5/1980 | Mattei | |
| 4,343,788 | A | 8/1982 | Mustacich et al. | |
| 4,849,228 | A * | 7/1989 | Yamamoto et al. ........... | 424/502 |
| 5,326,567 | A | 7/1994 | Capelli | |
| 5,780,658 | A * | 7/1998 | Martinez-Pardo et al. ..... | 554/51 |
| 5,869,073 | A | 2/1999 | Sawan et al. | |
| 5,916,585 | A * | 6/1999 | Cook et al. .................... | 424/426 |
| 6,294,183 | B1 * | 9/2001 | Ito et al. ........................ | 424/404 |
| 6,436,419 | B1 * | 8/2002 | Sun et al. ...................... | 424/404 |
| 6,468,521 | B1 | 10/2002 | Pedersen et al. | |
| 2002/0099113 | A1 * | 7/2002 | Rabasco et al. ............... | 523/122 |
| 2004/0142039 | A1 * | 7/2004 | Shalaby et al. ............... | 424/486 |
| 2004/0175429 | A1 * | 9/2004 | Alavattam et al. ............ | 424/490 |
| 2004/0258632 | A1 * | 12/2004 | Boyd et al. ..................... | 424/49 |
| 2005/0048124 | A1 | 3/2005 | Sarangapani | |
| 2005/0064210 | A1 | 3/2005 | McGhee et al. | |

FOREIGN PATENT DOCUMENTS

| | | | | |
|---|---|---|---|---|
| EP | 0272149 B1 | 3/1992 | | |
| WO | WO 02/30204 A1 | 4/2002 | | |
| WO | WO 03/043593 | 5/2003 | | |
| WO | WO 03/094638 | * 11/2003 | ............ | A23L 3/3517 |
| WO | WO 2006/125099 | 11/2006 | | |
| WO | WO 2006/125121 | 11/2006 | | |
| WO | WO 2006/125125 | 11/2006 | | |

OTHER PUBLICATIONS http://en.wikipedia.org/wiki/PLGA, last modified May 19, 2010, accessed May 19, 2010.*
Block, S.S., Disinfection, Sterilization, and Preservation 4th ed. 1991, pp. 225, 232, also pp. 233 and 313.
U.S. Appl. No. 11/389,824, filed Mar. 27, 2006.
U.S. Appl. No. 11/132,946, filed May 19, 2005.
U.S. Appl. No. 11/133,007, filed May 19, 2005.

* cited by examiner

*Primary Examiner* — Daniel Sullivan
*Assistant Examiner* — Peter Anthopolos
(74) *Attorney, Agent, or Firm* — Roberts Mlotkowski Safran & Cole, P.C.

(57) ABSTRACT

An antimicrobial composition comprising: a complex of an anionic polyester with an antimicrobial cationic surfactant, wherein the anionic polyester has at least one carboxylic group. A medical device having an antimicrobial composition comprising: a complex of an anionic polyester with an antimicrobial cationic surfactant wherein the anionic polyester has at least one carboxylic group.

8 Claims, No Drawings

ANTIMICROBIAL POLYMER COMPOSITIONS AND THE USE THEREOF

FIELD OF THE INVENTION

The present invention relates generally to polymer compositions and their use for making or coating articles, such as medical devices. More specifically the invention relates to antimicrobial compositions that are complexes of an anionic polymer with an antimicrobial cationic surfactant (M). Further, the present invention relates to complexes of anionic polyester with lauric arginate (LAE), which may be used alone or in combination with medical devices. The present invention also relates to medical devices utilizing such antimicrobial compositions.

BACKGROUND OF THE INVENTION

Whenever a medical device is used in a surgical setting, a risk of infection is created. The risk of infection dramatically increases for invasive or implantable medical devices, such as intravenous catheters, arterial grafts, intrathecal or intracerebral shunts and prosthetic devices, which create a portal of entry for pathogens while in intimate contact with body tissues and fluids. The occurrence of surgical site infections is often associated with bacteria that colonize on the medical device. For example, during a surgical procedure, bacteria from the surrounding atmosphere may enter the surgical site and attach to the medical device. Bacteria can use the implanted medical device as a pathway to surrounding tissue. Such bacterial colonization on the medical device may lead to infection and morbidity and mortality to the patient.

A number of methods for reducing the risk of infection associated with invasive or implantable medical devices have been developed that incorporate antimicrobial agents into the medical devices. Such devices desirably provide effective levels of antimicrobial agent while the device is being used.

WO 2003/043593 describes an antimicrobial system that uses an antimicrobial cationic surfactant derived from the condensation of fatty acids and esterified dibasic amino acids, as an antimicrobial activity enhancer, in combination with common antimicrobial agents. In particular, this reference describes the use of lauric arginate (LAE) in combination with 2,4,4'-trichloro-2'-hydroxy-diphenylether (triclosan), 3,4,4-trichlorocarbanilid (triclocarban), 2-phenoxyethanol, chlorhexidine salts, hexetidine and cetylpyridinium salts, for cosmetic formulations and preparations directed to avoid body odour and to provide oral care. This reference, however, is silent with respect to the use of LAE in connection with medical devices.

It would be beneficial to incorporate the antimicrobial cationic surfactant described above, either alone or in combination with common antimicrobial agents such as triclosan, triclocarban, 2-phenoxyethanol, chlorhexidine salts, hexetidine and cetylpyridinium salts, into an invasive or implantable medical device to reduce the risk of infection associated with such devices. Further, it is desirable to provide an antimicrobial composition where the release mechanism of LAE into the target environment is independent of the solubilization of the antimicrobial composition in the target environment, and that exhibits immediate activity upon contact with fluids in the human body.

SUMMARY OF THE INVENTION

The present invention is directed to an antimicrobial composition comprising a complex of an anionic polyester with an antimicrobial cationic surfactant wherein the anionic polyester is selected from the group consisting of an anionic polyester having at least one carboxylic group; a sulfonic acid polymer; and a phosphoric acid polymer.

More specifically, described herein is an antimicrobial composition comprising a complex of an anionic polyester with a cationic surfactant derived from the condensation of fatty acids and esterified dibasic amino acids, wherein the anionic polyester has at least one carboxylic acid group and the formula:

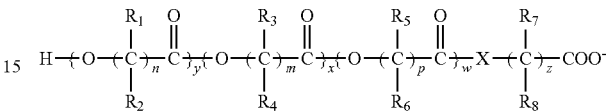

where $800 \geq x+y+w \geq 5$; $y \geq 0$; $x \geq 0$; $w \geq 0$; n, m, p and z independently range from about 1 to about 12; $R_1, R_2, R_3, R_4, R_5, R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

Additionally, described herein is an antimicrobial composition comprising a complex of an anionic polyester with an antimicrobial cationic surfactant, wherein the anionic polyester has the formula:

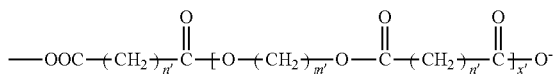

wherein $1 \geq n' \leq 13$; $1 \geq m' \leq 9$; and x' is the degree of polymerization and ranges from about 4 to about 50.

DETAILED DESCRIPTION

The present invention provides an antimicrobial composition comprising a complex of an anionic polymer with an antimicrobial cationic surfactant. In one embodiment, the antimicrobial composition comprises a complex of an anionic polyester with an antimicrobial cationic surfactant, wherein the anionic polyester has at least one carboxylic acid group that may be linear or branched. The complex typically comprises from about 5 wt. % to about 75 wt. % of the antimicrobial cationic surfactant.

The term "complex" as used herein refers to an intimate mixture at the molecular scale, preferably with ionic or covalent bonding between the antimicrobial cationic surfactant and the anionic polymer. The complex preferably comprises a salt formed between the anionic polymer and the antimicrobial cationic surfactant, but it may also comprise clusters and/or colloidals of the antimicrobial cationic surfactant.

The anionic polymer described herein may be an anionic polyester having at least one carboxylic acid group that may be linear or branched; a sulfonic acid polymer; or a phosphoric acid polymer and the like.

The anionic polyester may be absorbable or nonabsorbable, and may be synthesized via ring opening polymerization of aliphatic lactone monomers. Specifically, the aliphatic lactone monomers are polymerized in the presence of an organometallic catalyst and an initiator. Alternatively, the anionic polyester may be synthesized by condensation polymerization of a diol with diacid, wherein the molar ratio of the diol to the diacid is less than 1. Alternatively, the anionic polyester may be a synthesized anionic form of the reaction product of (a) a polyglycolic acid composition and (b) a polyester of diglycolic acid and a unhindered glycol, as described in more detail in U.S. Pat. Nos. 4,122,129 and 4,095,600, the content each of which is incorporated by reference as if set forth in its entirety; or a synthesized anionic form of the reaction product of (a) an aliphatic polyester of lactide, glycolide, epsilon-caprolactone, p-dioxanone, and trimethylene carbonate and (b) a poly(alkylene diglycolate) homopolymer or copolymer, as described in more detail in U.S. Pat. No. 5,644,002, the content of which is incorporated by reference as if set forth in its entirety.

Typical aliphatic lactone monomers that may be utilized to synthesize the anionic polyester described herein, and from which the repeat units of the anionic polyester are derived, are selected from the group consisting of glycolide, trimethylene carbonate, L-lactide, D-lactide, DL-lactide, mesolactide, epsilon-caprolactone, p-dioxanone, 1,3-dioxan-2-one, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

The organometallic catalysts include titanates and zirconates, and preferably organotin compounds such as stannous chloride and stannous octoate.

The initiators are desirably compounds containing at least one anionic group, such as a carboxylic acid group, and at least one other group such as a hydroxyl group or an amine. Typical initiators, suitable for the synthesis of an anionic polyester having carboxylic acid groups, are alpha-hydroxyl acids such as glycolic acid, D- lactic acid, DL-Lactic acid, L-lactic acid; β-hydroxyacids, γ-hydroxyacids, δ-hydroxyacids, and ε-hydroxyacids such as ε-hydroxycaproic acid. Preferable initiators contain at least one carboxylic acid group and a primary hydroxyl group, such as glycolic acid. The alcohol group readily participates in a reaction that incorporates the initiator in the growing chain. Typical initiators suitable for the synthesis of branched polyesters with at least one carboxylic acid group are the polyhydroxyacids, such as glucoronic acid.

In certain embodiments, the anionic polyester may have only one carboxylic acid group. Such anionic polyesters are described in U.S. Pat. Nos. 4,201,216 and 4,994,074, the entire content which is incorporated herein by reference, and may be generally represented by the following formula:

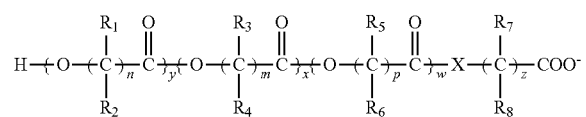
[A]

where 800=>x+y+w>=5; y>=0; x>=0; w>=0; n, m, p and z independently range from about 1 to about 12; $R_1$, $R_2$, $R_3$, $R_4$, $R_5$, $R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

The anionic polyesters include homopolymers and copolymers of lactide and glycolide, i.e., polylactide, polyglycolide, and copolymers of lactide and glycolide with each other and with other reactive monomers; poly(p-dioxanone); poly (alkylene oxalate); copolymers of vinyl acetates with unsaturated carboxylic acids such as crotonic, acrylic and methacrylic acids; and mixtures of such polymers. Particularly preferred polymers are the copolymers of lactide and glycolide, which contain from about 15 to 85% lactide, and have an inherent viscosity of from about 0.5 to 4.0 measured as a 0.1 percent solution in hexafluoroisopropanol at 25° C. These polymers are water-insoluble, rapidly absorbable, and soluble in many common organic solvents such as acetone, chloroform, toluene, xylene, and 1,1,2-trichloroethane.

It is also possible to produce other anionic polyesters in a similar fashion with terpolymers, tetramers, and the like, from building blocks including, but not limited to, glycolide, lactide, epsilon-caprolactone, trimethylene carbonate, and p-dioxanone.

Specific examples of such anionic polyesters are represented by formulae IA, IIA and IIIA.

The anionic polyester of Formula IA is a copolymer of epsilon-caprolactone and glycolide that is formed by using glycolic acid as an initiator and stannous octoate as the catalyst. The polymerization may be conducted in a batch process that allows the formation of a random copolymer. However, it is also possible to conduct the polymerization in such a way as to allow for the formation of a semi-block copolymer. The initiator ratio may be varied to allow one to obtain a molecular weight that makes the final copolymer in a useable form. The term "initiator ratio" as used herein, refers to the total moles of monomer divided by the total moles of initiator. For example, the initiator ratio may range from about 5 to about 600, corresponding to a Mn of about 575 to about 69,000, respectively. When the anionic polyester is used to prepare a coating on a substrate such as a medical device, the initiator ratio may range from about 10 to 30, corresponding to a Mn of about 1,150 to about 3,450, respectively. The size of the copolymer can vary greatly depending on its ultimate application.

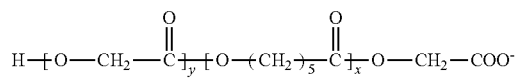
[IA]

anionic alpha-hydroxy, omega-carboxy poly(epsilon-caprolactone co-glycolide)
where x ranges from about 5 to about 190; y ranges from about 5 to about 190; and x+y<=200.

The anionic polyester represented by Formula IIA is a poly-(epsilon-caprolactone) that is polymerized with glycolic acid as an initiator, and is consequently terminated with a carboxylic acid group. For example, the initiator ratio may range from about 5 to about 600, corresponding to a Mn of about 575 to about 69,000, respectively. When the anionic polyester is used to prepare a coating on a substrate such as a medical device, the initiator ratio ranges from about 10 to about 30, corresponding to a Mn of about 1,150 to about 3,450, respectively.

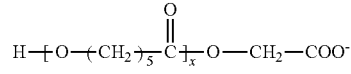
[IIA]

anionic alpha-hydroxy, omega-carboxy poly(epsilon-caprolactone) where x ranges from about 10 to about 200.

The anionic polyester represented by Formula IIIA is a copolymer formed from lactide and glycolide with glycolic acid as an initiator. The initiator ratio ranges from about 10 to about 200, which corresponds to a Mn of about 1,170 to about 28,800, respectively.

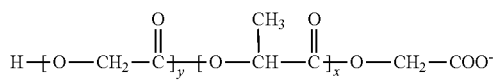
[IIIA]

anionic alpha-hydroxy, omega-carboxy poly(glycolide co-lactide) where x ranges from about 5 to about 190; y ranges from about 5 to about 190; and x+y<=200.

Where the number of carboxylic acid groups is desirably 2 or more, one can provide an initiator that will cause the anionic polyester to form, for example, a branched structure. Examples of such initiators include, but are not limited to, tartaric acid, citric acid and the like. The branched structure may have one or more carboxylic acid groups in one or more branches on the polymer backbone or side chain. They may even be in the form of a dendrimer or star structure.

In an alternative embodiment, the anionic polyester may have more than one carboxylic acid groups as represented by Formula A'. For example, copolymers of adipic acid and 1,4 butanediol disclosed in U.S. Pat. No. 3,942,532 may be synthesized in an anionic form as represented by Formula IVA', which is an anionic polyester that is rich in carboxylic acid groups and adipate.

[A']

—OOC—(CH$_2$)$_{n'}$—C(=O)—[O—(CH$_2$)$_{m'}$—O—C(=O)—(CH$_2$)$_{n'}$—C(=O)]$_{x'}$—O- wherein 1>=n'<=13; 1>=m'<=9; and x' is the degree of polymerization and ranges from about 4 to about 50.

A specific example of such an anionic polyester is polytetramethylene adipate diacid represented by Formula IVA'

[IVA']

—OOC—(CH$_2$)$_4$—C(=O)—[O—(CH$_2$)$_4$—O—C(=O)—(CH$_2$)$_4$—C(=O)]$_{x'}$—O- where x' ranges from about 4 to about 50. The value of x' depends on the molar ratio of diol to diacid and the extent of the conversion of the limiting reactant, where the molar ratio of the diol to the diacid is less than 1.

Examples of the diol that may be used to synthesize the anionic polyester of Formula IVA' include, but are not limited to, ethylene glycol, propylene glycol, butanediol, pentanediol, hexanediol, nonanediol, decanediol, undecanediol, dodecanediol, or mixtures thereof. Examples of the diacid include, but are not limited to, succinic, glutaric, adipic, pimelic, suberic, azelaic, sebacic acid, or mixtures thereof. The diols and diacids, upon reaction, may be condensed to obtain a polyester suitable for application as, for example, a substrate coating. Polyesters of the Formula A' may have a molecular weight in the range of approximately 200 to 10,200, preferably 1,000 to 15,000.

The antimicrobial cationic surfactant described herein is derived from the condensation of fatty acids and esterified dibasic amino acids. A particular example of such an antimicrobial cationic surfactant is lauric arginate (LAE—manufactured by Lamirsa Laboratories, Barcelona, Spain). Lauric arginate, a cationic preservative derived from lauric acid and arginine, in particular, the ethyl ester of the lauramide of the arginine monohydrochloride, can be used to protect against the growth of microorganisms. The chemical structure of LAE is described in formula (I):

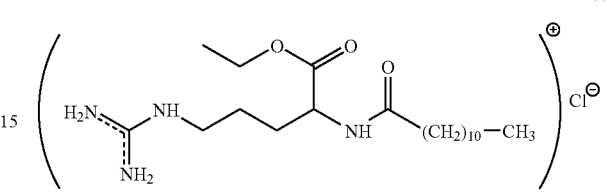
(I)

The complex of an anionic polyester and an antimicrobial cationic surfactant may be made by treating an anionic polyester with a solution of the source of the antimicrobial cationic surfactant. For example, the anionic polyester may be in the form of solid fibers, sheet, sponge or fabric. In certain embodiments, the anionic polyester is an ion exchanger. In other embodiments, the anionic polyester may be in free acid form, in which case for example, the source of the antimicrobial cationic surfactant may be a salt of a weak acid, whereby the anionic polyester is at least partially complexed by the antimicrobial cationic surfactant. When using an antimicrobial cationic surfactant, for example, the antimicrobial cationic surfactant is exchanged for a proton on the anionic polyester and part of the antimicrobial cationic surfactant is converted to a weak acid. The mixture of weak acid and salt in the solution results in a buffered solution which maintains a fairly constant pH and controls the degree of exchange reaction. An equilibrium reaction is established whereby the antimicrobial cationic surfactant is bound to the acid portion of the polyester and also to the salt molecules. Similar processes are described in EP-A-0437095, the entire content of which is expressly incorporated herein by reference.

The exchange reaction can be carried out in water or alcohol alone but is preferably carried out in mixtures of water and alcohols. The use of a mixture of water and alcohol provides good solubility for weak acid salts, and the alcohol enhances the ability of the anionic polyester to swell during the exchange reaction. Thus the physical properties (e.g. the inherent mechanical strength) of the anionic polyester are retained. Isopropyl alcohol is the preferred alcohol because many of the above-mentioned antimicrobial cationic surfactants have good solubility therein in combination with water. Preferably, the alcohol to water molar ratio is in the range of about 9:1 to 1:9. Linear and branched C2-C12 mono- or polyalcohols, including, but not limited to, n-propyl alcohol and ethanol, are suitable alcohols.

The amount of the antimicrobial cationic surfactant used is generally about equal to or up to twice the stoichiometric amount of carboxylic acid content of the polyester. Alternatively, a second charge of a stoichiometric amount of antimicrobial cationic surfactant can be used if the reaction is recharged with fresh solvent and salt after the first charge reaches a constant pH. The material with elevated pH is then washed to remove the excess antimicrobial cationic surfactants.

The present invention provides an antimicrobial composition comprising a complex of an anionic polyester with an antimicrobial cationic surfactant, wherein the complex comprises from about 5 wt. % to about 75 wt. % of the antimicrobial cationic surfactant, and preferably from about 10 wt. % to about 60 wt. % of antimicrobial cationic surfactant, more preferably from about 20 wt. % to about 50 wt. % of antimicrobial cationic surfactant.

Accordingly, the complexes of the anionic polyesters previously described in Formulae A, A', and IA to IVA and the antimicrobial cationic surfactant, are represented by the following:

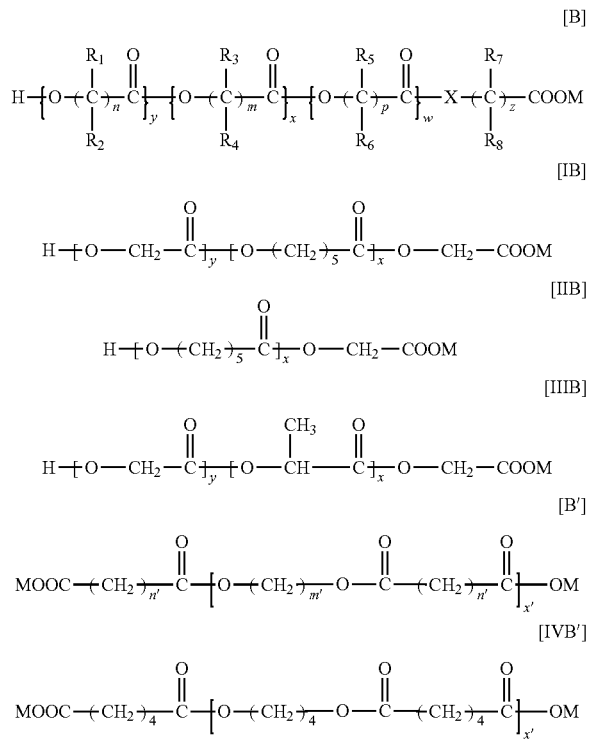

The antimicrobial composition of the present invention provide the advantage of varying release kinetics for the antimicrobial cationic surfactant. These varying release kinetics allow for an initial release of the antimicrobial cationic surfactant that provides antimicrobial activity immediately upon insertion in an aqueous environment, followed by a continual, extended release of the antimicrobial cationic surfactant from the composition.

In a further aspect, the antimicrobial composition may optionally contain other components that improve the antimicrobial effectiveness of the composition, or that otherwise serve as active agents for other benefits. These components include, but are not limited to, additional antimicrobials, additional salts, any other excipients or active ingredients that provide the compositions with beneficial properties or enhance the antimicrobial activity of the compositions. Such components include, but are not limited to, antimicrobial agents such as triclosan, triclocarban, 2-phenoxyethanol, chlorhexidine salts, hexetidine and cetylpyridinium salts; antibiotics; and other active ingredients.

The antimicrobial compositions described herein may be used to coat substrate materials. Additionally, they can be a part of the coating that contains the antimicrobial composition described herein. These coatings may comprise either a single layer or multiple layers. In another embodiment, the antimicrobial composition may also be applied to a preformed article or part of an article of manufacture as a coating. The coated article may be produced, for example, by dipping the article into the composition, coextruding the article, wire coating the article, or spraying the article with the composition and then drying the coated article.

The antimicrobial composition may be made separately, and then applied as a coating to a substrate such as a medical device. Alternately, the antimicrobial composition may be made in situ, for example, by first coating a substrate such as a medical device with the anionic polyester followed by in situ treatment with a solubilized salt of the antimicrobial cationic surfactant, thus imparting antimicrobial properties to the substrate.

Additionally, organic liquids such as organic solvents may be utilized to facilitate complexation of the antimicrobial cationic surfactant and the anionic polyester.

The antimicrobial compositions described herein are used alone or in combination with other polymer coatings to provide advantageous properties to the surface of the substrate. These compositions can also be used, to deliver pharmaceutical agents that, for example, are antiinfective, anticoagulants, improve healing, are antiviral, antifungal, antithrombogenic or impart other properties to coated substrates.

The antimicrobial compositions are also used to inhibit algae, fungal, mollusk, or microbial growth on surfaces. The antimicrobial compositions described herein may also used as herbicides, insecticides, antifogging agents, diagnostic agents, screening agents, and antifoulants.

In another aspect, the present invention includes an article of manufacture that is a medical device that comprises the antimicrobial compositions described herein. In one embodiment, the antimicrobial composition can be used to form an article or a portion of the article, for example by spinning, molding, casting, or extrusion.

The antimicrobial composition can be utilized to manufacture a medical device including, but not limited to a fiber, mesh, powder, microspheres, flakes, sponge, foam, fabric, nonwoven, woven mat, a film, suture anchor device, suture, staple, surgical tack, clips, plate and screw, drug delivery device, adhesion prevention barrier, and tissue adhesive.

The medical device may be composed of one or more of the antimicrobial compositions of the present invention, alone or in combination with other polymeric components.

As discussed above, the antimicrobial cationic surfactant may be incorporated into the anionic polyester in an aqueous alcohol environment. The term "incorporate", "incorporated", or "incorporating", as used herein, refers to combining the antimicrobial cationic surfactant with the anionic polyester by physical or chemical means. In one embodiment, the antimicrobial cationic surfactant may be incorporated into the anionic polyester prior to forming a substrate such as a medical device. In an alternative embodiment, the antimicrobial cationic surfactant can be incorporated into the anionic polyester after the formation of a substrate such as a medical device. For instance, the anionic polyester may be impregnated with the antimicrobial cationic surfactant by dipping, soaking, spraying or coating a medical device with the cationic surfactant dispersed in an aqueous alcohol environment, as shown in Examples below.

EXAMPLE 1

Inventive

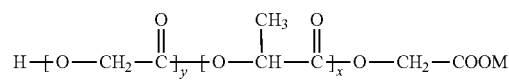

where M=lauric arginate (LAE)

A L(−) lactide/glycolide copolymer containing 65 mole % lactide and 35 mole % glycolide was synthesized with a glycolic acid initiator using about 107.9 moles of monomers per mole of glycolic acid, and with a 0.33 molar stannous octoate catalyst to form the anionic polyester.

A 0.54 gram aliquot of the anionic polyester was dissolved in 10.92 grams of ethyl acetate. Into the solution was added 0.27 grams of a 10.5% by weight solution of LAE in ethanol containing traces of water. This yielded a solution containing the complex formed between LAE and the anionic polyester. The amount of LAE in the complex of the anionic polyester and LAE was 5% by weight based on the weight of the anionic polyester.

To the above solution of the complex was added 0.54 grams of calcium stearate, which was then subjected to high shear. A 2/0 polyglactin 910 suture was coated by immersion. The remaining solvent was evaporated and the suture was vacuum dried at room temperature, yielding a suture with a coating loading of 4.86% by weight.

The antimicrobial efficacy was evaluated by in vitro bacterial colonization assay, in which a section of a control suture having a coating of anionic polyester without LAE and 5 cm sections of the suture having a coating of the antimicrobial composition were exposed to an *E. coli* suspension in 20% serum in saline for 24 hours. After incubation, the suture sections were rinsed with sterile saline to remove free bacteria. The suture sections were then placed in TSA (Trypticase soy agar BBL), and incubated at 37° C. for 24 hrs to allow *E. coli* bacteria that were attached to the suture sections to developed into visible colonies. No bacterial colonies were found on the suture sections having a coating of the antimicrobial composition, while the control suture sections (having a coating of the copolymer without LAE) showed visible colonies of *E. coli* on the suture.

EXAMPLE 2

Inventive

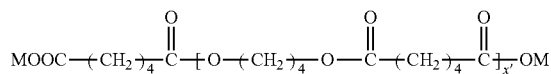

where M=lauric arginate (LAE)

Polytetramethylene adipate diacid was prepared by reacting 1,4-butanediol (BD) with adipic acid (AA) at a molar ratio of 0.85 BD/AA to form the anionic polyester. 0.27 grams of the anionic polyester was dissolved in 11.261 grams of ethyl acetate and admixed for two hours with 0.514 grams of a solution containing 10.5% of LAE in ethanol with traces of water. The amount of LAE in the complex of the anionic polyester and LAE was 16.65% by weight based on the weight of the anionic polyester.

A size 0 Mersilene® suture was coated with the above coating solution yielding a suture with 0.98% by wt. coating level. Four sections of 0.25 cm of the suture were placed into a Petri dish side-by-side and contiguous. An inoculum suspension was prepared in 20% serum in saline. 10 ul of the inoculum suspension having $10^4$ cfu per four suture section was added on top of the suture sections in the Petri dish. After exposure of the suture sections to the inoculum suspension at room temperature for 30 minutes. Surviving bacteria were recovered by pouring TSA (Trypticase soy agar BBL) into the Petri dish and incubated at 37° C. for 24 hr. The antimicrobial efficacy of the suture coated with the antimicrobial composition is a 2.3 log reduction of viable bacteria against *S. aureus* and a 3.2 log reduction against *P. aeruginosa*.

What is claimed is:

1. An antimicrobial composition comprising: an ionic salt complex of an anionic polyester with lauric arginate, where the anionic polyester has the formula:

[IIIA]

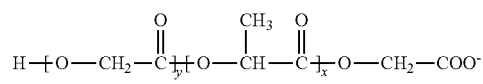

wherein x is between 5 and 190, y is between 5 to 190, and x+y≤200.

2. The antimicrobial composition according to claim 1, wherein the anionic polyester is prepared from a ring-opening polymerization of lactide and glycolide in the presence of an organometallic catalyst and an anionic initiator selected from the group consisting of glycolic acid, D-lactic acid, DL-lactic acid and L-lactic acid.

3. The antimicrobial composition according to claim 2, wherein the anionic initiator is glycolic acid.

4. The antimicrobial composition of claim 1, wherein the amount of lauric arginate in the complex is from about 5% to about 75% by weight based on the weight of the anionic polyester.

5. The antimicrobial composition of claim 1, wherein the amount of lauric arginate in the complex is from about 10% to about 60% by weight based on the weight of the anionic polyester.

6. The antimicrobial composition of claim 1, wherein the amount of lauric arginate in the complex is from about 20% to about 50% by weight based on the weight of the anionic polyester.

7. A method of making an ionic salt complex of an anionic polyester of the formula:

[IIIA]

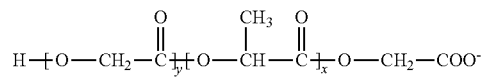

wherein x is between 5 and 190, y is between 5 to 190, and x+y≤200, with lauric arginate, comprising the step of incorporating an effective amount of the lauric arginate with the anionic polyester in an aqueous soluble alcohol.

8. The method of claim 7 wherein the aqueous soluble alcohol is selected from the group consisting of ethanol, n-propyl alcohol, and isopropyl alcohol.

* * * * *

UNITED STATES PATENT AND TRADEMARK OFFICE
CERTIFICATE OF CORRECTION

| | | |
|---|---|---|
| PATENT NO. | : 8,840,876 B2 | Page 1 of 1 |
| APPLICATION NO. | : 11/132543 | |
| DATED | : September 23, 2014 | |
| INVENTOR(S) | : Erneta et al. | |

It is certified that error appears in the above-identified patent and that said Letters Patent is hereby corrected as shown below:

Title page under item (12) "Eemeta" should read -- Erneta --

Title page item (75) should read, Inventors: Modesto ERNETA
　　　　　　　　　　　　　　　　　　　　　Robert DiLuccio
　　　　　　　　　　　　　　　　　　　　　Xintian Ming Signed and Sealed this
Thirteenth Day of January, 2015

Michelle K. Lee
*Deputy Director of the United States Patent and Trademark Office*